(12) United States Patent
Mehdi et al.

(10) Patent No.: US 6,372,903 B1
(45) Date of Patent: Apr. 16, 2002

(54) METHOD FOR PREPARING POLYAZACYCLOALKANES GRAFTED ON SILICA GEL AND USE OF GRAFTED COMPOUNDS

(75) Inventors: Ahmad Mehdi, Montpellier; Franck Denat; Frédéric Barbette, both of Dijon; Roger Guilard, Fontaine les Dijon; Gilles Lagrange, Forges les Bains, all of (FR)

(73) Assignees: Commissariat a l'Energie Atomique, Paris; L'Air Liquide, Societe Anonyme pour l'Etude et l'Exploitation des Procedes Georges Claude, Paris Cedex, both of (FR)

( * ) Notice: Subject to any disclaimer, the term of this patent is extended or adjusted under 35 U.S.C. 154(b) by 0 days.

(21) Appl. No.: 09/600,996
(22) PCT Filed: Jan. 22, 1999
(86) PCT No.: PCT/FR99/00127
§ 371 Date: Jul. 26, 2000
§ 102(e) Date: Jul. 26, 2000
(87) PCT Pub. No.: WO99/37399
PCT Pub. Date: Jul. 29, 1999

(30) Foreign Application Priority Data

Jan. 26, 1998 (FR) .............................. 98 00784

(51) Int. Cl.⁷ ..................... C07D 255/02; C07D 257/02
(52) U.S. Cl. ...................................... 540/474; 540/483
(58) Field of Search ............................... 540/460, 474, 540/483

(56) References Cited

U.S. PATENT DOCUMENTS 5,891,574 A * 4/1999 Guilard et al. .............. 428/404

FOREIGN PATENT DOCUMENTS

FR 2789380 A1 * 8/2000
WO WO-96/11056 A1 * 4/1996

\* cited by examiner

*Primary Examiner*—John M. Ford
(74) *Attorney, Agent, or Firm*—Young & Thompson

(57) ABSTRACT

The invention concerns a method for preparing polyazacyloalkanes immobilised on a silica gel from a polyazacycloalkane of formula (A) in which: $R_1$ and $R_2$ represent a hydrogen atom, an alkyl radical, or a [hetero(aryl)]alkyl radical; $W_1$, $W_2$ and $W_3$ represent a radical of formula (B): —[$(CT_1T_2)_n$—$[N(R_3)]_p$—$(CT_3T_4)_m$]$_l$— such as defined in the description; $R_3$ represents a hydrogen atom, an alkyl radical or a [hetero(aryl)]alkyl radical, provided that the polyazacycloalkane ring of the compound of formula (A) comprises not more than 30 cyclic carbon atoms, and not more than 6 cyclic nitrogen atoms. The invention is characterised in that: (a) the compound of formula (A) is reacted with a compound of formula (C): Z—$R_4$—$Si(X_1)(X_2)(X_3)$, such as defined in the description to form a compound of formula (D); (b) said compound of formula (D) is condensed on the silanol sites of a silica gel to form the immobilised polyazacycloalkane of formula (E); and (c) some ethanol sites having not reacted are, if required, protected by Z', a group protecting the hydroxyl function. The invention is useful for separating oxygen from air.

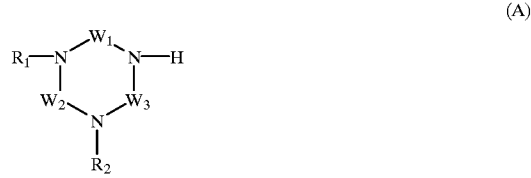

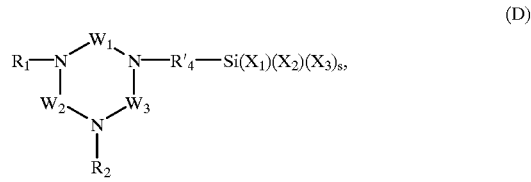

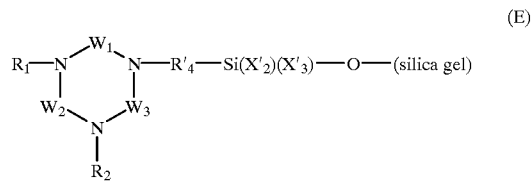

13 Claims, No Drawings

METHOD FOR PREPARING POLYAZACYCLOALKANES GRAFTED ON SILICA GEL AND USE OF GRAFTED COMPOUNDS

Polyazamacrocyclic compounds are of considerable interest in the field of coordination chemistry. These ligands in particular form stable complexes with transition elements and heavy metals (Bradshaw J. S, Krakowiak K. E, Izatt R. M, Aza-crown Macrocycles in *The Chemistry of Heterocyclic Compounds*; edited by Taylor E. C, John Wiley & Son Inc.: New York, 1993, pp. 1–885; Izatt R. M, Pawlak K, Bradshaw J. S, Bruening R. L, *Chem. Rev.*, 1995, 95, 2529–2586). The dimensions of the macrocyclic cavity, the shape and the rigidity of the ring, the size of the chelated ring, and the number and the nature of the substituents carried by the nitrogen atoms are all factors which influence the affinity of the ligand with respect to a given metal ion and thus the selectivity with respect to other elements. These properties have made possible the use of these compounds in fields as varied as the selective coordination of atmospheric dioxygen (Cabani S. *React. and Funct. Polym.*, 1996, 167–182; Machida R, Kimura E, Kodama M, *Inorg. Chem.*, 1983, 22, 2055–2061), medical imaging (Alexander V, *Chem. Rev.*, 1995, 95, 273–342) or the extraction of metal elements (Guilard, R, Chollet H, Guiberteau P, Cocolios P, WO 96/11189, published on Apr. 18, 1996, FR 2725382 published on Apr. 12, 1996; Izatt R. M, Bruening R. L, Borup M. B, *Water Sci. Technol.*, 1991, 23, 301–308).

In the field of the extraction of heavy metals and of the purification of effluents, the major disadvantage of these nitrogenous macrocycles is their solubility both in water and organic solvents, which results in a loss of the ligand when it is used in a liquid—liquid extraction process. On the other hand, the immobilization of the ligand on a solid support makes possible the development of a solid-liquid extraction process which exhibits numerous advantages, such as a reduced cost (no loss of the ligand), the noncontamination of the solvents to be purified, and easy use and regeneration of the columns. In the context of gas separation or purification, it is known, for example, that tetraazamacrocyclic cobalt complexes exhibit a high affinity with respect to dioxygen. However, the superoxide oxygen-comprising species formed can change in the direction of species of $\mu$-peroxo type which have a limited lifetime in solution, where they undergo irreversible decomposition reactions (Martell A. E, Basak A. K, Raleigh C. J, *Pure Appl. Chem.*, 1988, 60, 1325–1329). The attachment of the active complex to a solid matrix results in the superoxide species, which promotes the reversibility of the reaction and limits the decomposition of the oxygen-comprising species. Thus, absorption/desorption cycles might be carried out by lowering the pressure and/or raising the temperature.

Some industrial sectors, for example electronics, use liquids or gases of very high purity and environmental standards are becoming increasingly strict. Consequently, the development of processes which make it possible to remove trace amounts constitutes a priority. To this end, numerous modified polymers possessing selective chelating properties have been developed. Silica gels are among the most widely used supports (Biernat J. F, Konieczka P, Tarbet B. J, Bradshaw J. S, Izatt R. M, *Sep. Purif. Methods*, 1994, 23, 77–348). This is because they exhibit numerous advantages with respect to organic polymers: they are inexpensive, mechanically and thermally stable, inert with respect to numerous chemicals and insoluble in most organic solvents and can be easily modified.

Various silica gels modified by polyazamacrocyclic ligands have already been synthesized (Gros C, Rabiet F, Denat F, Brandes S, Chollet H, Guilard R, *J. Chem. Soc. Dalton Trans.*, 1996, 1209–1214; Subba Rao Y. V, De Vos D. E, Bein T, Jacobs P. A, *Chem. Commun.*, 1997, 355–356; Bagnoud M. A, Haerdi W, Veuthey J. L, *Chromatographia*, 1990, 29, 495–499; Izatt R. M, Bruenig R. L, Tarbet B. J, Griffin L. D, Bruening M. L, Krakowiak K. E, Bradshaw J. S, *Pure Appl. Chem.*, 1990, 62, 1115–1118; Dudler V, Lindoy L. F, Sallin D, Schlaepfer C. W, *Aust. J Chem.*, 1987, 40, 1557–1563). The most commonly used synthetic route (route A) is represented diagrammatically as follows:

During a first stage, a spacer arm carrying an electrophilic ending is attached to the silica gel by reaction of the appropriate silylated reactant (generally an alkoxysilane) with the silanol sites. Various assembling groups, such as those which appear hereinabove, can thus be used. The unreacted silanol sites can optionally be protected by the action of trimethylchlorosilane, in order to increase the selectivity of the gel or the hydrophobic nature of the latter. The desired macrocycle is subsequently condensed onto the modified silica gel. In a final stage, the grafted macrocycle can be N-substituted by the action of an appropriate electrophilic reactant. The amount of macrocycle grafted according to this synthetic scheme is approximately 0.35–0.40 mmol/g of material.

Another possible route of access to modified silica gels of this type (route B) consists, in a first stage, in functionalizing the macrocycle with the spacer arm, the grafting onto the silica subsequently taking place in a final stage: Bradshaw et al. (Izatt R. M, Bruening R. L, Tarbet B. J, Griffin L. D, Bruening M. L, Krakowiak K. E, Bradshaw J. S, *Pure Appl. Chem.*, 1990, 62, 1115–1118, Bradshaw J. S, Krakowiak K. E, Tarbet B. J, Bruening R. L, Griffin L. D, Cash D. E, Rasmussen T. D, Izatt R. M, *Solv. Extract Ion Exch.*, 1989, 7, 855–864) have thus developed a method which makes it possible to graft pentaazamacrocycles and various mixed (oxygen-nitrogen) macrocycles onto a silica gel, represented diagrammatically as follows:

In a first stage, a substituent carrying a terminal ethylene unit is attached to the desired macrocycle. The compound is subsequently hydrosilylated and the product thus obtained is condensed onto the silica gel.

However, the first synthetic route (A) exhibits two major disadvantages:

Only 30 to 50% of the spacer arms grafted in the first stage react with the macrocycle. The amount of grafted macrocycles is thus greatly reduced thereby and the residual presence of the unreacted functional groups can prove to be harmful during the implementation of a process using these materials for a given application.

The N-functionalization of the grafted tetraazamacrocycle, the final stage in the synthesis, is not quantitative as only one to two secondary amine functional groups of the three available react with the electrophilic reactant. In addition, some macrocycles may be bonded by two nitrogen atoms to the silica gel. This heterogeneity is harmful to the effectiveness and to the selectivity of the modified silica gel.

The synthetic route (B), while it makes it possible to control the substitution of the grafted ligand, is problematic to carry out, however, and it requires the use of expensive catalysts, such as hexachloroplatinic acid. The subject-matter of the present invention provides an unexpected solution to the problems set out hereinabove.

A subject-matter of the invention is a process for the preparation of a polyazacycloalkane, immobilized on a silica gel, from a polyazacycloalkane of formula (A):

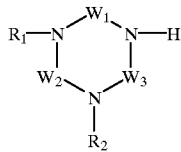
(A)

in which
R$_1$ and R$_2$, which are identical or different, each represent, independently of one another, a hydrogen atom, a linear or branched alkyl radical comprising from 1 to 15 carbon atoms, W$_1$, W$_2$ and W$_3$, which are identical or different, represent, independently of one another, a divalent radical chosen from those represented by the general formula (B):

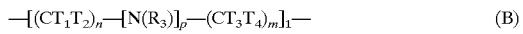
(B)

in which
p represents an integer equal to 1 or equal to 0,
l represents an integer equal to 1 or to 2,
n and m, which are identical or different, each represent, independently of one another, an integer less than or equal to 3 and greater than or equal to 1,
T$_1$, T$_2$, T$_3$ and T$_4$, which are identical or different, either each represent, independently of one another, a hydrogen atom, a linear or branched alkyl radical comprising from 1 to 15 carbon atoms or else CT1T2 and/or CT3T4 represent the divalent group —(C=O)—,
R3 represents, independently of R1 or R2, a hydrogen atom, a liner or branched alkyl radical comprising from 1 to 15 carbon atoms,
which comprises:
a) the reaction of the compound of formula (A) with a compound of formula (C)

Z—R$_4$—Si(X$_1$)(X$_2$)(X$_3$)     (C)

in which:
X$_1$, X$_2$ and X$_3$, which are identical or different, each represent, independently of one another, a hydrogen atom, a halogen atom or an OR$_5$ radical, in which R$_5$ represents a hydrogen atom or an alkyl radical comprising from 1 to 4 carbon atoms,
R$_4$ represents a divalent radical derived from a saturated or unsaturated aliphatic hydrocarbonaceous chain comprising from 1 to 10 carbon atoms, in which chain are optionally inserted one or more structural links chosen from the arylene group or the —O—, —S—, —O—C(=O)—, —N(R$_6$)—C(=O)— or —N(R$_6$)— fragments, in which fragments R$_6$ represents a hydrogen atom, an aliphatic hydrocarbonaceous radical comprising from 1 to 6 carbon atoms, a benzyl radical or a phenethyl radical, the said chain being unsubstituted or substituted by one or more radicals chosen from halogen atoms, the hydroxyl group, alkyl radicals comprising from 1 to 4 carbon atoms or the benzyl or phenethyl radicals, and
Z represents a functional group capable of reacting with the secondary amine functional group, =N—H, to form an N—C covalent bond, to form a compound of formula (D),

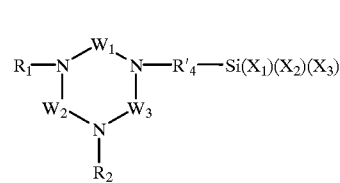
(D)

in which R'$_4$ represents either R$_4$ as defined above, or R$_4$ substituted by a radical originating from the reaction of Z with the secondary amine group =N—H,
b) the condensation of said compound of formula (D) with silanol sites of a silica gel, to form the immobilized polyazacycloalkane of formula (E):

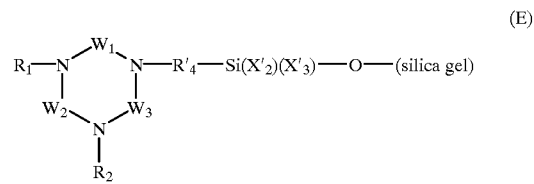
(E)

in which:
X'$_2$ represents X$_2$ as defined above or O-(silica gel), and
X'$_3$ represents X$_3$ as defined above or O-(silica gel);
c) and the protection, if desired, of all or a portion of the free unreacted silanol sites with Z', a protective group for the hydroxyl functional group.

The term "polyazacycloalkane of formula (A)" denotes non-immobilized polyazacycloalkanes known to a person skilled in the art at the date of filing of the present patent application.

When the compound of formula (A) comprises three cyclic nitrogen atoms, it is in particular 1,4,7-triazacyclononane, 1,4,7-triazacyclodecane or 1,4,8-triazacyclododecane.

When the compound of formula (A) comprises four cyclic nitrogen atoms, it is in particular 1,4,7,10-tetraazacyclododecane (cyclene), 1,4,7,10-tetraazacyclotridecane, 1,4,7,11-tetraazacyclotetradecane, 1,4,8,11-tetraazacyclotetradecane (cyclam), 1,4,8,12-tetraazacyclopentadecane, 1,5,9,13-tetraazacyclohexadecane or 1,5,10,14-tetraazacyclooctadecane.

When the compound of formula (A) comprises five cyclic nitrogen atoms, it is in particular 1,4,7,10,13-pentaazacyclopentadecane, 1,4,7,11,15-pentaazacyclooctadecane or 1,5,9,13,17-pentaazacyclooctadecane.

When the compound of formula (A) comprises six cyclic nitrogen atoms, it is in particular 1,4,7,10,13,16-hexaazacyclooctadecane or 1,5,9,13,17,20-hexaazacyclotetracosane.

The compound of formula (A) can be unsubstituted or substituted; when it is substituted, the substituents are chosen from those which do not react under the operating conditions with the compound of formula (B); examples of substituted polyazacycloalkanes are those substituted by alkyl radicals comprising from 1 to 15 carbon atoms or the benzyl, picolyl or phenethyl radicals, such as 6-dodecyl-1,4,8,11-tetraazacyclotetradecane, 3-dodecyl-1,5,9,13-tetraazacyclohexadecane, 3-dodecyl-1,5,10,14-tetraazacyclooctadecane, 5,5,7,12,12,14-hexamethyl-1,4,8,11-tetraazacyclotetradecane, 1,4,7,10,13-pentaethyl-1,4,7, 10,13,16-hexaazacyclooctadecane, 1,7,10-tetraethyl-1,4,7,
10,13-pentaazacyclopentadecane, 1-methyl-1,4,8,11-
tetraazacyclotetradecane, 1-benzyl-1,4,8,11-
tetraazacyclotetradecane, 1-[(2-pyridyl)-methyl]-1,4,8,11-
tetraazacyclotetradecane, 1-[(3-pyridyl)methyl]-1,4,8,11-
tetraazacyclotetradecane or 1,4-dibenzyl-1,4,8,11-
tetraazacyclotetradecane.

The term "functional group capable of reacting with a secondary amine" denotes in particular those which react according to a nucleophilic substitution mechanism, such as, for example, the halogen radicals and particularly the iodo radical, or those which react according to an electrophilic addition mechanism, such as, for example, the epoxy functional group, which results in an N—$CH_2$—CH(OH) fragment; it can also be a free, salified or esterified carboxyl functional group or a $CH_2$=CH— group, which results in an N—$CH_2$—$CH_2$— fragment via a reaction of "Michael" type according to a nucleophilic addition mechanism. These examples do not have a limiting nature and it is obvious that any functional group known to a person skilled in the art at the date of filing of the present patent application as being capable of reacting with a secondary amine functional group to form an N—CH covalent bond forms an integral part of the present description of the invention.

The term "protective group for the hydroxyl functional group" denotes, for Z', any group resulting from an etherification or esterification reaction with Si—OH; mention may in particular be made, as example of Z' group, of the trialkylsilyl radical in which each of the alkyl radicals comprises, independently of one another, from 1 to 4 carbon atoms.

According to a first specific aspect of the process as defined above, the latter is carried out with a compound of formula ($C_1$):

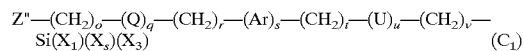
                                                                                  ($C_1$)

corresponding to the formula (C) in which Z—$R_4$ represents the radical:

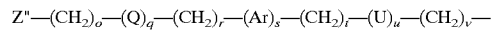

in which:
- Z" represents either a halo radical or an $R_7$O—C(=O)— group, in which $R_7$ represents a hydrogen atom, a sodium atom, a potassium atom or a radical chosen from alkyl radicals comprising from 1 to 4 carbon atoms or the tosyl, mesyl or trifluoromethylsulfonyl radicals, or an oxiran-2-yl group or an ethenyl group,
- o, r, t and v, which are identical or different, represent, independently of one another, an integer greater than or equal to 0 and less than or equal to 6,
- Q and U, which are identical or different, represent, independently of one another, an oxygen atom, a sulfur atom or one of the —O—CO—, —CO—O—, —NH—CO—, —CO—NH— or —NH— groups,
- q, s and u, which are identical or different, represent, independently of one another, an integer greater than or equal to 0 and less than or equal to 1,
- Ar represents an arylene radical and in particular a phenylene radical, it being understood that:
- when q is equal to 1, o is other than 0,
- when q is equal to 1 and when u is equal to 0, the sum r+s+t+v is other than 0,
- when u is equal to 1, v is other than 0,
- when u is equal to 1 and when q is equal to 0, the sum o+r+s+t is other than 0,
- when s is equal to 0 and when q and u are each equal to 1, the sum r+t is other than 0, and
- the sum o+r+t+v is less than or equal to 12.

The process which is the subject-matter of the present invention is carried out in particular with a compound of formula ($C_2$), corresponding to the formula ($C_1$) as defined above in which:
- Z" represents a bromo radical, an iodo radical or an oxiran-2-yl radical,
- ($X_1$), ($X_2$) and ($X_3$) each represent an ethoxy radical or a methoxy radical,
- the sum of o+r+t+v is less than or equal to 6 and
- the sum of q+u is less than or equal to 1.

The process is carried out in particular with the following products:
- (triethoxy)(3-iodopropyl)silane,
- 2-[[[3-(triethoxysilyl)propyl]oxy]methyl]-oxirane and
- N-[[4-(bromomethyl)phenyl]methyl]-N-[3-(triethoxysilyl)propylamine.

The compounds of formulae (C) and ($C_1$) are obtained from commercially available products by methods known to a person skilled in the art.

According to another specific aspect of the process as defined above, the latter is carried out from a compound of formula ($A_1$), corresponding to the formula (A) as defined above in which:
- $W_1$, $W_2$ and $W_3$, which are identical or different, represent, independently of one another, a divalent radical chosen from those represented by the general formula ($B_1$):

                                                                                   ($B_1$)

in which:
- n and m are, independently of one another, equal to 2 or to 3 and p is equal to 0 or to 1.

The process is carried out in particular from a compound of formula ($A_2$), corresponding to the formula ($A_1$) in which the $R_1$ and $R_2$ radicals each represent a hydrogen atom, and more particularly from cyclam, a compound of formula ($A_2$) as defined above in which $W_1$ represents the divalent radical —$(CH_2)_3$—NH—$(CH_2)_2$—, $W_2$ represents the divalent radical —$(CH_2)_2$— and $W_3$ represents the divalent radical —$(CH_2)_3$—, or from cyclene, a compound of formula ($A_2$) in which $W_1$ represents the divalent radical —$(CH_2)_2$—NH—$(CH_2)_2$— and $W_2$ and $W_3$ each represent the divalent radical —$(CH_2)_2$—.

In an alternative form of the process which is a subject-matter of the present invention, the compound of formula ($D_1$), corresponding to the formula (D) as defined above in which at least one of the $R_1$, $R_2$ or $R_3$ radicals represents a hydrogen atom, is functionalized beforehand on one or more of its cyclic nitrogens to form a compound of formula (D')

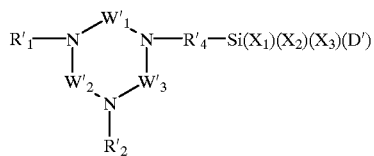

in which:
R'₄, X₁, X₂ and X₃ are as defined above,
R'₁ and R'₂, which are identical or different, represent, independently of one another, a hydrogen atom, a linear or branched alkyl radical comprising from 1 to 15 carbon atoms, a [hetero(aryl)]alkyl radical comprising from 7 to 12 carbon atoms or a —(CH₂)ᵥᵥ—C(=O)—V radical in which V represents one of the OH, NH₂ or OR₈ radicals, in which R₈ represents an alkyl radical comprising from 1 to 4 carbon atoms, and w represents an integer greater than or equal to 1 and less than or equal to 6;

W'₁, W'₂ and W'₃, which are identical or different, represent, independently of one another, a divalent radical chosen from those represented by the general formula (B'):

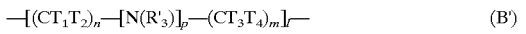

in which:
p, l, n, m, T₁, T₂, T₃ and T₄ have the same meanings as those defined above for the formula (B),
R'₃ represents, independently of R'1 or R'2, a hydrogen atom, a linear or branched alkyl radical comprising from 1 to 15 carbon atoms, or a
—(CH₂)ᵥᵥ—C(=O)—V radical in which V represents one of the OH, NH₂ or OR₈ radicals, in which R₈ represents an alkyl radical comprising from 1 to 4 carbon atoms, and w represents an integer greater than or equal to 1 and less than or equal to 6,
it being understood that at least one of the R'₁, R'₂ or R'₃ radicals represents a —(CH₂)ᵥᵥ—C(=O)—V radical,
before being grafted onto the silanol sites of the silica gel to form an immobilized and functionalized macrocycle of formula (E'), corresponding to the formula (E) in which R₁, R₂ and R₃ represent R'₁, R'₂ and R'₃ respectively.

When this alternative form of the process which is the subject-matter of the present invention is carried out, it is preferable to prepare a compound of formula (D'₁), corresponding to the formula (D') as defined above in which none of the R'₁, R'₂ or R'₃ radicals represents a hydrogen atom.

This alternative variant of the process is carried out in a particularly appropriate way from the compound of formula (A₂) as defined above, which results in the compound of formula (D₂), corresponding to the formula (D) in which W₁, W₂, W₃, R₁ and R₂ are as defined in the formula (A₂), and then in the compound of formula (D'₂), corresponding to the formula (D') as defined above in which R'₁, R'₂ and R'₃ each represent a —(CH₂)ᵥᵥ—C(=O)—OR'₈ radical, in which w' is equal to 1, 2 or 3 and R'₈ represents a hydrogen atom, a methyl radical or an ethyl radical.

The reactions for functionalizing the NH group are known to a person skilled in the art; one of them is disclosed in the international patent application published under No. WO96/11189 on Apr. 18, 1996.

Another subject-matter of the invention is the compounds of formulae (D) and (D') as defined above, in particular the compounds of formulae (D₁), (D₂), (D'₁) and (D'₂) as defined above, and more particularly the following products:

1-[3-(triethoxysilyl)propyl]-1,4,7,10-tetraazacyclododecane,
1-[3-(triethoxysilyl)propyl]-1,4,7,10-tetraazacyclotridecane,
1-[3-(triethoxysilyl)propyl]-1,4,8,11-tetraazacyclotetradecane,
1-[3-(triethoxysilyl)propyl]-1,4,8,12-tetraazacyclopentadecane,
1-[3-(triethoxysilyl)propyl]-1,5,9,13-tetraazacyclohexadecane,
1-[2-hydroxy-3-[[3-(triethoxysilyl)propyl]oxy]-propyl]-1,4,7,10-tetraazacyclododecane,
1-[2-hydroxy-3-[[3-(triethoxysilyl)propyl]oxy]-propyl]-1,4,7,10-tetraazacyclotridecane,
1-[2-hydroxy-3-[[3-(triethoxysilyl)propyl]oxy]-propyl]-1,4,8,11-tetraazacyclotetradecane,
1-[2-hydroxy-3-[[3-(triethoxysilyl)propyl]oxy]-propyl]-1,4,8,12-tetraazacyclopentadecane,
1-[2-hydroxy-3-[[3-(triethoxysilyl)propyl]oxy]-propyl]-1,5,9,13-tetraazacyclohexadecane,
1-[[4-[[[-3-(triethoxysilyl)propyl]amino]-methyl]phenyl]methyl]-1,4,7,10-tetraazacyclododecane,
1-[[4-[[[-3-(triethoxysilyl)propyl]amino]-methyl]phenyl]methyl]-1,4,7,10-tetraazacyclotridecane,
1-[[4-[[[-3-(triethoxysilyl)propyl]amino]-methyl]phenyl]methyl]-1,4,8,11-tetraazacyclotetradecane,
1-[[4-[[[-3-(triethoxysilyl)propyl]amino]-methyl]phenyl]methyl]-1,4,8,12-tetraazacyclopentadecane,
1-[[4-[[[-3-(triethoxysilyl)propyl]amino]-methyl]phenyl]methyl]-1,5,9,13-tetraazacyclohexadecane,
ethyl 10-[3-(triethoxysilyl)propyl]-1,4,7,10-tetraazacyclododecane-1,4,7-tripropanoate,
ethyl 10-[3-(triethoxysilyl)propyl]-1,4,7,10-tetraazacyclotridecane-1,4,7-tripropanoate,
ethyl 11-[3-(triethoxysilyl)propyl]-1,4,8,11-tetraazacyclotetradecane-1,4,8-tripropanoate,
ethyl 12-[3-(triethoxysilyl)propyl]-1,4,8,12-tetraazacyclopentadecane-1,4,8-tripropanoate,
ethyl 13-[3-(triethoxysilyl)propyl]-1,5,9,13-tetraazacyclohexadecane-1,5,9-tripropanoate,
ethyl 10-[2-hydroxy-3-[[3-(triethoxysilyl)-propyl]oxy]propyl]-1,4,7,10-tetraazacyclododecane-1,4,7-tripropanoate,
ethyl 10-[2-hydroxy-3-[[3-(triethoxysilyl)-propyl]oxy]propyl]-1,4,7,10-tetraazacyclotridecane-1,4,7-tripropanoate,
ethyl 11-[2-hydroxy-3-[[3-(triethoxysilyl)-propyl]oxy]propyl]-1,4,8,11-tetraazacyclotetradecane-1,4,8-tripropanoate,
ethyl 12-[2-hydroxy-3-[[3-(triethoxysilyl)-propyl]oxy]propyl]-1,4,8,12-tetraazacyclopentadecane-1,4,8-tripropanoate,
ethyl 13-[2-hydroxy-3-[[3-(triethoxysilyl)-propyl]oxy]propyl]-1,5,9,13-tetraazacyclohexadecane-1,5,9-tripropanoate,
ethyl 10-[[4-[[[3-(triethoxysilyl)propyl]-amino]methyl]phenyl]methyl]-1,4,7,10-tetraazacyclododecane-1,4,7-tripropanoate,
ethyl 10-[[4-[[[3-(triethoxysilyl)propyl]-amino]methyl]phenyl]methyl]-1,4,7,10-tetraazacyclotridecane-1,4,7-tripropanoate,
ethyl 11-[[4-[[[3-(triethoxysilyl)propyl]-amino]methyl]phenyl]methyl]-1,4,8,11-tetraazacyclotetradecane-1,4,8-tripropanoate,
ethyl 12-[[4-[[[3-(triethoxysilyl)propyl]-amino]methyl]phenyl]methyl]-1,4,8,12-tetraazacyclopentadecane-1,4,8-tripropanoate, and
ethyl 13-[[4-[[[3-(triethoxysilyl)propyl]-amino]methyl]phenyl]methyl]-1,5,9,13-tetraazacyclohexadecane-1,5,9-tripropanoate.

An example of the implementation of the process according to the invention is illustrated by the following schemes:

Iodopropyltriethoxysilane is synthesized simply by the action of NaI on commercial chloropropyltriethoxysilane. The iodopropyltriethoxysilane, in solution in acetonitrile, is then added dropwise to a solution of cyclam in acetonitrile at reflux in the presence of $Na_2CO_3$. The reaction mixture is maintained at reflux for 24 h, the solvent is subsequently evaporated and pentane is added to the residue. The excess insoluble cyclam is filtered off, the filtrate is concentrated and compound 1 is obtained without subsequent purification with a yield of 50%. The grafting of 1 onto the silica gel is carried out at reflux of the xylene for 4 days. The amount of grafted macrocycles is then 0.8 mmol/g of modified silica gel.

Compound 1 can be functionalized and then subsequently grafted according to the scheme:

Compound 1 is stirred for 4 days at room temperature in ethyl acrylate. After evaporating the ethyl acrylate and washing several times with pentane, the product 2 is obtained quantitatively. The grafting of 2 onto the silica gel is subsequently carried out as described above.

If this methodology is compared with that which proceeds by grafting the spacer group onto the silica gel and then by attaching the desired ligand to this arm, this novel process makes it possible to double the amount of tetraazamacrocycles grafted at the surface of the silica gel. The number of "active sites" per unit of surface area is thus significantly increased, resulting in a considerable improvement in the effectiveness of the material. The second advantage, which is even more important, is to be able to completely control the nature of the ligand attached, since it is synthesized, isolated and characterized before grafting.

This novel method for the synthesis of ligands carrying the spacer arm does not require special experimental conditions and results, with suitable yields, in the expected compounds without subsequent purification. In addition, this synthesis is carried out in a single stage and not two as in the methodology involving the hydrosilylation of the terminal alkene. Finally, the N-substitution of these novel ligands is quantitative and makes possible the grafting of completely N-substituted macrocycles.

This method applies not only to the compound of formula (A) as defined above but also to linear polyamines. Various spacer arms (comprising aromatic units or ester or amide functional groups) can be used. The electrophilic reactant used during the N-functionalization can also vary, making possible access to a large range of silica gels exhibiting an optimum effectiveness and an optimum selectivity.

The macrocycles grafted onto a silica gel by the process which is the subject-matter of the present invention are used for removing metal cations from a liquid, in particular removing cations chosen from U, Pu, Am, Ce, Eu, Al, Gd, Cr, Mn, Fe, Co, Ni, Cu, Zn, Ag, Cd, Sn, Au, Hg or Pb.

The macrocycles grafted onto a silica gel by the process which is the subject-matter of the present invention are also used to prepare complexes with transition metals, said transition metal complexes being used for the separation and the removal of oxygen from a gas mixture, such as air, comprising it.

The following examples illustrate the invention without, however, limiting it.

Synthesis of (triethoxy)(3-iodopropyl)silane.

36.5 g (0.243 mol) of sodium iodide (dried at 100° C. under 1 mm Hg for 24 h) are dissolved, under an argon atmosphere, in 150 ml of acetone which has been dried and distilled over a 4 Å molecular sieve. 58.6 g (0.243 mol) of chloropropyltriethoxysilane are then added dropwise and the reaction mixture is brought to reflux for 24 h. The white sodium chloride precipitate formed is then filtered off and the solvent is evaporated. The residue is distilled and the iodopropyltriethoxysilane is obtained in the form of a slightly yellow liquid (46.6 g, 58%) (B.p.: 120–125° C./1 mm Hg).

$^1$H NMR ($\delta$ ppm $CDCl_3$): 0.70 (m, 2H), 1.20 (t, 9H), 1.91 (m, 2H), 3.19 (t, 2H), 3.80 (q, 6H). $^{13}$C NMR ($\delta$ ppm $CDCl_3$): 11.11, 13.14, 19.00, 28.42, 59.21.

Synthesis of 1-[3-(triethoxysilyl)propyl]-1,4,8,11-tetraazacyclotetradecane (compound 1)

72 g (0.359 mol) of cyclam and 15 g of $Na_2CO_3$ (dried at 100° C. under 1 mm Hg for 24 h) are placed in 2.5 l of acetonitrile in a 6 l reactor under a stream of nitrogen. The mixture is brought to reflux, a solution of 24.2 g (0.073 mol) of iodopropyltriethoxysilane in 500 ml of acetonitrile is then added dropwise and then the reaction mixture is maintained at reflux for 48 h. After evaporating the solvent on a rotary evaporator (still under a nitrogen atmosphere), pentane is added to the residue and the excess cyclam is filtered off. This operation is repeated three times, the filtrates are combined, the pentane is evaporated and compound 1 is obtained in the form of a colorless oil (15 g, 50.8%).

$^1$H NMR ($\delta$ ppm $CDCl_3$): 0.46 (m, 2H), 1.10 (t, 9H), 1.43 (m, 2H), 1.59 (m, 4H), 2.30–2.70 (m, 18H), 3.69 (q, 6H). $^{13}$C NMR ($\delta$ ppm $CDCl_3$): 8.64, 18.91, 26.92, 29.55, 48.35, 48.66, 49.60, 49.99, 50.08, 51.57, 53.92, 55.17, 56.05, 58.88. Elemental analysis: for ($C_{19}H_{44}N_4O_3Si$); Calculated: C: 56.39%; H: 10.96%; N: 13.84%; Found: C: 56.13%; H: 11.01%; N: 12.76%.

Synthesis of ethyl 11-[3-(triethoxysilyl)-propyl]-1,4,8,11-tetraazacyclotetradecane-1,4,8-tripropanoate (compound 2)

8.2 g (0.020 mol) of 1 and 70 ml of ethyl acrylate are stirred at room temperature for 4 days under an argon atmosphere. After evaporating the excess ethyl acrylate and washing 3 times with pentane, compound 2 is obtained in the form of a yellow oil (14 g, 100%).

$^1$H NMR ($\delta$ ppm $CDCl_3$): 0.55 (m, 2H), 1.19 (t, 12H) , 1.23 (t, 12H) , 1.54 (m, 6H) , 2.48 (m, 24H) , 2.71 (m, 6H), 3.78 (q, 6H), 4.09 (q, 6H). $^{13}$C NMR ($\delta$ ppm $CDCl_3$): 7.94, 14.21, 18.28, 20.46, 23.89, 31.03, 32.65, 50.63 (broad), 51.18 (broad), 58.21, 60.14. Elemental analysis: for ($C_{34}H_{68}N_4O_9Si$): Calculated : C: 57.92%; H: 9.73%; N: 7.95%; Found : C: 57.67%; H: 9.90%; N: 8.19%.

Grafting onto silica gel

The silica gel (Kieselgel 60, diameter 0.2–0.5 mm, specific surface 550 $m^2/g$, Merck) is dried beforehand by azeotropic distillation in xylene. The macrocycle and the silica gel (1.5 mmol per 1 g) are mixed and brought to reflux of the xylene (10 ml per 1 g of silica) for 4 days. The silica gel is subsequently filtered off, washed successively with xylene, water, acetone and ethyl ether, and finally dried.

The percentage analysis of the nitrogen in the silica gels thus modified makes it possible to determine the amount of grafted macrocycle:

for compound 1: 0.81 mmol per gram of material;

for compound 2: 0.60 mmol per gram of material.

The presence of the ester functional groups on the cyclam in compound 2 results in a larger increase in mass, explaining the lower amount of macrocycle per gram of material.

What is claimed is:

1. A process for the preparation of a polyazacycloalkane, immobilized on a silica gel, from a polyazacycloalkane of formula (A):

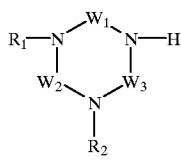
(A)

in which
R$_1$ and R$_2$, which are identical or different, each represent, independently of one another, a hydrogen atom, a linear or branched alkyl radical having from 1 to 15 carbon atoms,
W$_1$, W$_2$ and W$_3$, which are identical or different, represent, independently of one another, a divalent radical chosen from those represented by the general formula (B$_1$):

$$-(CH_2)_n-(NH)_p-(CH_2)_m-\qquad (B_1)$$

in which:
n and m are, independently of one another, equal to 2 or to 3 and p is equal to 0 or to 1,
it being understood that the polyazacycloalkane nucleus of the compound of formula (A) has at most 30 cyclic carbon atoms and at most 6 cyclic nitrogen atoms, which comprises:
a) the reaction of the compound of formula (A) with a compound of formula (C$_1$)

in which
Z' represents either a halo radical or an R$_7$O—C(=O)— group, in which R$_7$ represents a hydrogen atom, a sodium atom, a potassium atom or a radical chosen from alkyl radicals having from 1 to 4 carbon atoms or the tosyl, mesyl or trifluoromethylsulfonyl radicals, or an oxiran-2-yl group or an ethenyl group,
o, r, t and v, which are identical or different, represent, independently of one another, an integer greater than or equal to 0 and less than or equal to 6,
Q and U, which are identical or different, represent, independently of one another, an oxygen atom, a sulfur atom or one of the —O—CO—, —CO—O—, —NH—CO—, —CO—NH— or —NH— groups,
q, s and u, which are identical or different, represent, independently of one another, an integer greater than or equal to 0 and less than or equal to 1,
Ar represents a phenylene radical,
it being understood that:
when q is equal to 1, o is other that 0,
when q is equal to 1 and when u is equal to 0, the sum r+s+t+v is other than 0,
when u is equal to 1, v is other than 0,
when u is equal to 1 and when q is equal to 0, the sum o+r+s+t is other than 0,
when s is equal to 0 and when q and u are equal to 1, the sum r+t is other than 0,
the sum o+r+t+v is less than or equal to 12, and
X$_1$, X$_2$ and X$_3$, which are identical or different, each represent, independently of one another, a hydrogen atom, a halogen atom or an OR$_5$ radical, in which R$_5$ represents a hydrogen atom or an alkyl radical having from 1 to 4 carbon atoms,
to form a compound of formula (D),

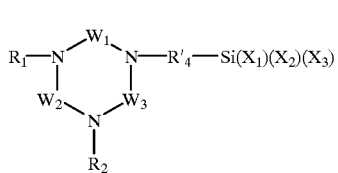

in which R'$_4$ represents either R$_4$ wherein R$_4$ represents a divalent radical derived from a chain having from 1 to 10 carbon atoms, in which chain are optionally inserted one or more structural links chosen from the arylene group or the —O—, —S—, —O—C(=O)—, —N(R$_6$)—C(=O)— or —N(R$_6$)— fragments, in which fragments R$_6$ represents a hydrogen atom, an aliphatic hydrocarbonaceous radical comprising from 1 to 6 carbon atoms, a benzyl radical or a phenethyl radical, the said chain being unsubstituted or substituted by one or more radicals chosen from halogen atoms, the hydroxyl group, alkyl radicals comprising from 1 to 4 carbon atoms or the benzyl or phenethyl radicals, or R$_4$ substituted by a radical originating from the reaction of Z" with the secondary amine group =N—H,
b) the condensation of said compound of formula (D) with silanol sites of a silica gel, to form the immobilized polyazacycloalkane of formula (E):

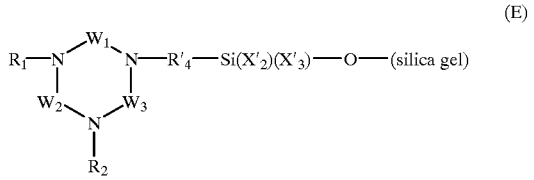

in which:
X'$_2$ represents X$_2$ as defined above or O-(silica gel), and
X'$_3$ represents X$_3$ as defined above or O-(silica gel);
c) and the protection, if desired of some of the unreacted silanol sites with Z', a protective group for the hydroxyl functional group, to form the immobilized polyazacycloalkane of formula (E'), corresponding to the formula (E) in which all or a portion of the free —OH sites of the silica gel are blocked in the form of OZ' sites and in particular in the form of (trialykl) silyloxy sites.

2. The process as defined in claim 1, wherein use is made, in stage a), of the compound of formula (C$_2$), corresponding to said formula (C$_1$) in which:
X$_1$, X$_2$ and X$_3$, which are identical or different, each represent, independently of one another, a hydrogen atom, a halogen atom or an OR$_5$ radical, in which R$_5$ represents a hydrogen atom or an alkyl radical having from 1 to 4 carbon atoms,
Z" represents a bromo radical, an iodo radical or an oxiran-2-yl radical,
(X$_1$), (X$_2$) and (X$_3$) each represent an ethoxy radical or a methocy radical, the sum o+r+t+v is less than or equal to 6 and the sum q+u is less than or equal to 1 and in particular of (triethoxy) (3-iodopropyl)-silane, 2-[[[3-(triethoxysilyl)propyl]oxy]methyl]-oxirane or N-[[4-(bromomethyl)phenyl]methyl]-N-[3-(triethoxysilyl)propyl]amine.

3. The process as defined in claim 1, wherein use is made, in stage a), of the compound of formula (A$_2$), corresponding to formula (A$_1$) in which the R$_1$ and R$_2$ radicals each represent a hydrogen atom, and wherein use is in particular made, in stage a), of cyclam or cyclene.

4. The process as defined in claim 1, in which the compound of formula (D$_1$), corresponding to the formula (D) as defined above in which at least one of the R$_1$, R$_2$ or R$_3$ radicals represents a hydrogen atom, is substituted on one or more of its cyclic nitrogens to form a compound of formula (D')

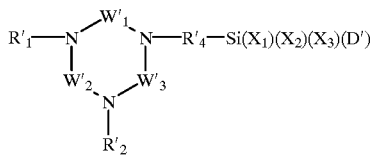

in which:

R'$_4$, X$_1$, X$_2$ and X$_3$ are as defined above,

R'$_1$ and R$_2$, which are identical or different, represent, independently of one another, a hydrogen atom, a linear or branched alkyl radical having from 1 to 15 carbon atoms or a —(CH$_2$)$_w$—C(=O)—V radical in which V represents one of the OH, NH$_2$ or OR$_8$ radicals in which R$_8$ represents an alkyl radical having from 1 to 4 carbon atoms, and w represents an integer greater than or equal to 1 and less than or equal to 6;

W'$_1$, W'$_2$ and W'$_3$, which are identical or different, represent, independently of one another, a divalent radical chosen from those represented by the general formula (B'):

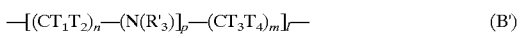

in which:

p, l, n, m, T$_1$, T$_2$, T$_3$ and T$_4$ have the same meanings as those defined above for the formula (B), R'$_3$ represents, independently of R'$_1$ or R'$_2$, a hydrogen atom, a linear or branched alkyl radical having from 1 to 15 carbon atoms or a —(CH$_2$)$_w$—C(=O)—V radical in which V represents one of the OH, NH$_2$ or OR$_8$ radicals, in which R$_8$ represents an alkyl radical having from 1 to 4 carbon atoms, and w represents an integer greater than or equal to 1 and less than or equal to 6, it being understood that at least one of the R'$_1$, R'$_2$ or R'$_3$ radicals represents a —(CH$_2$)$_w$—C(=O)—V radical, before being grafted onto the silanol sites of the silica gel to form an immobilized and functionalized macrocycle of formula (E'), corresponding to the formula (E) in which R$_1$, R$_2$ and R$_3$ represent R'$_1$, R'$_2$ and R'$_3$ respectively.

5. The process as defined in claim 4, wherein a compound of formula (D'$_1$) is prepared, which formula corresponds to the formula (D') in which none of the R'$_1$, R'$_2$ or R'$_3$ radicals represents a hydrogen atom.

6. The process as defined in claim 5, wherein use is made, in stage a), of the compound of formula (A$_2$) and wherein the preparation is carried out of a compound of formula (D'$_2$), corresponding to the formula (D') as defined above in which R'$_1$, R'$_2$ and R'$_3$ each represent a —(CH$_2$)$_{w'}$—C(=O)—OR'$_8$ radical in which w' is equal to 1, 2 or 3 and R'$_8$ represents a hydrogen atom, a methyl radical or an ethyl radical.

7. The compound of formula (D), as defined in claim 1.

8. The compound of formula (D') as defined in claim 4.

9. The compounds with the following names:

1-[3-(triethoxysilyl)propyl]-1,4,7,10-tetraazacyclododecane,

1-[3-(triethoxysilyl)propyl]-1,4,7,10-tetraazacyclotridecane,

1-[3-(triethoxysilyl)propyl]-1,4,8,11-tetraazacyclotetradecane,

1-[3-(triethoxysilyl)propyl]-1,4,8,12-tetraazacyclopentadecane,

1-[3-(triethoxysilyl)propyl]-1,5,9,13-tetraazacyclohexadecane,

1-[2-hydroxy-3-[[3-(triethoxysilyl)propyl]oxy]-propyl]-1,4,7,10-tetraazacyclododecane, 1-[2-hydroxy-3-[[3-(triethoxysilyl)propyl]oxy]-propyl]-1,4,7,10-tetraazacyclotridecane, 1-[2-hydroxy-3-[[3-(triethoxysilyl)propyl]oxy]-propyl]-1,4,8,11-tetraazacyclotetradecane, 1-[2-hydroxy-3-[[3-(triethoxysilyl)propyl]oxy]-propyl]-1,4,8,12-tetraazacyclopentadecane, 1-[2-hydroxy-3-[[3-(triethoxysilyl)propyl]oxy]-propyl]-1,5,9,13-tetraazacyclohexadecane, 1-[[4-[[[3-(triethoxysilyl)propyl]amino]-methyl]phenyl]methyl]-1,4,7,10-tetraazacyclododecane, 1-[[4-[[[3-(triethoxysilyl)propyl]amino]-methyl]phenyl]methyl]-1,4,7,10-tetraazacyclotridecane, 1-[[4-[[[3-(triethoxysilyl)propyl]amino]-methyl]phenyl]methyl]-1,4,8,11-tetraazacyclotetradecane, 1-[[4-[[[3-(triethoxysilyl)propyl]amino]-methyl]phenyl]methyl]-1,4,8,12-tetraazacyclopentadecane, 1-[[4-[[[3-(triethoxysilyl)propyl]amino]-methyl]phenyl]methyl]-1,5,9,13-tetraazacyclohexadecane, ethyl 10-[3-(triethoxysilyl)propyl]-1,4,7,10-tetraazacyclododecane-1,4,7-tripropanoate, ethyl 10-[3-(triethoxysilyl)propyl]-1,4,7,10-tetraazacyclotridecane-1,4,7-tripropanoate, ethyl 11-[3-(triethoxysilyl)propyl]-1,4,8,11-tetraazacyclotetradecane-1,4,8-tripropanoate, ethyl 12-[3-(triethoxysilyl)propyl]-1,4,8,12-tetraazacyclopentadecane-1,4,8-tripropanoate, ethyl 13-[3-(triethoxysilyl)propyl]-1,5,9,13-tetraazacyclohexadecane-1,5,9-tripropanoate, ethyl 10-[2-hydroxy-3-[[3-(triethoxysilyl)-propyl]oxy]propyl]-1,4,7,10-tetraazacyclododecane-1,4,7-tripropanoate, ethyl 10-[2-hydroxy-3-[[3-(triethoxysilyl)-propyl]oxy]propyl]-1,4,7,10-tetraazacyclotridecane-1,4,7-tripropanoate, ethyl 11-[2-hydroxy-3-[[3-(triethoxysilyl)-propyl]oxy]propyl]-1,4,8,11-tetraazacyclotetradecane-1,4,8-tripropanoate, ethyl 12-[2-hydroxy-3-[[3-(triethoxysilyl)-propyl]oxy]propyl]-1,4,8,12-tetraazacyclopentadecane-1,4,8-tripropanoate, ethyl 13-[2-hydroxy-3-[[3-(triethoxysilyl)-propyl]oxy] propyl]-1,5,9,13-tetraazacyclohexadecane-1,5,9-tripropanoate, ethyl 10-[[4-[[[3-(triethoxysilyl)propyl]-amino]methyl] phenyl]methyl]-1,4,7,10-tetraazacyclododecane-1,4,7-tripropanoate, ethyl 10-[[4-[[[3-(triethoxysilyl)propyl]-amino]methyl] phenyl]methyl]-1,4,7,10-tetraazacyclotridecane-1,4,7-tripropanoate, ethyl 11-[[4-[[[3-(triethoxysilyl)propyl]-amino]methyl] phenyl]methyl]-1,4,8,11-tetraazacyclotetradecane-1,4,8-tripropanoate, ethyl 12-[[4-[[[3-(triethoxysilyl)propyl]-amino]methyl] phenyl]methyl]-1,4,8,12-tetraazacyclopentadecane-1,4,8-tripropanoate, and ethyl 13-[[4-[[[3-(triethoxysilyl)propyl]-amino]methyl] phenyl]methyl]-1,5,9,13-tetraazacyclohexa-decane-1,5,9-propanoate.

10. The compound of formula ($D_1$) as defined in claim 4.
11. The compound of formula ($D_2$) as defined in claim 6.
12. The compound of formula ($D'_1$) as defined in claim 5.
13. The compound of formula ($D'_2$) as defined in claim 6.

* * * * *